United States Patent [19]

Debregeas et al.

[11] Patent Number: 5,385,739
[45] Date of Patent: Jan. 31, 1995

[54] STABLE COMPOSITIONS OF GASTROPROTECTED OMERPRAZOLE MICROGRANULES AND PROCESS FOR THE PRODUCTION THEREOF

[75] Inventors: Patrice Debregeas, Versailles; Gérard Leduc, Malesherbes, both of France

[73] Assignee: Ethypharm, Madrid, Spain

[21] Appl. No.: 78,548

[22] Filed: Jun. 16, 1993

[30] Foreign Application Priority Data

Jun. 16, 1992 [FR] France ................ 92 07249

[51] Int. Cl.$^6$ .................... A61K 9/54; A61K 9/62
[52] U.S. Cl. .................... 424/494; 424/458; 424/461; 424/462; 424/490; 424/493; 424/497
[58] Field of Search ........... 424/461, 462, 493, 494, 424/497

[56] References Cited

U.S. PATENT DOCUMENTS 4,255,431  4/1979  Junggren et al. ............ 424/263
4,840,799  6/1989  Appelgren et al. ........... 424/493

FOREIGN PATENT DOCUMENTS 0247983  2/1987  European Pat. Off. .
237506   9/1987  European Pat. Off. .
0470047  5/1992  European Pat. Off. .

OTHER PUBLICATIONS

Omeprazole, A Survey of Preclinical Data, The Scandinavian Journal of Gastroenterology, 1985, 113-120, Cederberg.
Acta Chemica Scandinavia, 43 (1989), 536-548 (Arne Brändstrom et al.).

Primary Examiner—G. S. Kishore
Assistant Examiner—James M. Spear
Attorney, Agent, or Firm—Dressler, Goldsmith, Shore & Milnamow, Ltd.

[57] ABSTRACT

The present invention relates to a stable formulation of omeprazole microgranules containing a neutral core consisting of sugar and starch, characterized in that it contains an active layer consisting of a dilution of omeprazole in mannitol in substantially equal amounts. It also relates to a process for producing such formulations.

8 Claims, No Drawings

STABLE COMPOSITIONS OF GASTROPROTECTED OMERPRAZOLE MICROGRANULES AND PROCESS FOR THE PRODUCTION THEREOF

The present invention relates to a pharmaceutical formulation of omeprazole in the form of gastroprotected microgranules having a stability over time compatible with pharmaceutical requirements and to the process for the manufacture of the said microgranules.

Omeprazole, or 5-methoxy-2-[[(4-methoxy-3,5-dimethyl-2-pyridyl)methyl]sulfinyl]-1H-benzimidazole, an anti-ulcerative substance which reduces gastrointestinal acid secretion, is well known and has been described especially in Swedish Patent No. 78 04231 (Aktiebolaget Hässle Fack).

It is also known that omeprazole has a very low solubility in water but that it is, in contrast, very soluble in alkaline solutions and that it degrades very quickly in acidic medium. Its degradation half-life is ten minutes in aqueous solutions with a pH of less than 4, eighteen hours for a pH equal to 6.5 and approximately 300 days for a pH of 11.

When omeprazole is used orally, it is consequently indispensable to gastroprotect the pharmaceutical form of the active material (gelatin capsules, tablets or powder) so as to prevent any contact of the latter in acidic medium in the stomach while achieving rapid dissolution in the intestinal medium, where the omeprazole must be absorbed, that is to say as soon as ambient pH becomes greater than 6.8.

The in vitro dissolution characteristics of an oral omeprazole formulation as well as the bioavailability results achieved in man with the aid of these oral formulations, consisting of protected granules, have been described in the Scandinavian Journal of Gastroenterology (1985; 20 (suppl. 108): 113–120, Pilbran A., Cederberg C.).

However, it was observed that the conventional enteric granules did not have a sufficient stability over time to be used in a satisfactory pharmaceutical form (gelatin capsules or tablets of microgranules) since degradation of the active principle is rapidly observed when they are placed under usual conditions of use (room temperature of 25° C., degree of humidity between 40 and 75%) with the appearance of harmful degradation products, such as described, for example, in Acta Chemica Scandinavia, 43 (1989), 536–548 (Arne Brändstrom et al.).

In order to overcome these disadvantages, it has especially been proposed (EP-A-0,247,983, Hässle A-G) to mix a suitable amount of omeprazole and of an alkaline sodium, potassium, magnesium or calcium salt or alkaline ammonium salts in a mass of cellulose coating derivatives and of disintegrating agents, so as to produce, by extrusion, a core whose composition is buffered and has an alkaline pH between 7 and 12.

The microgranules thus prepared are then conventionally gastroprotected and correspond to the dissolution and gastroresistance standards defined for an optimum use of the product orally, that is to say a dissolution greater than 75% after 30 minutes in an aqueous medium with a pH equal to 6.8 and a gastroresistance greater than 85% after 2 hours in a medium with a pH equal to 1.2.

Nevertheless, this type of preparation has a number of significant disadvantages, both from the technical and from the economic viewpoint. First of all, it is necessary to prepare combinations of products and mixtures, with risks of overall toxicity and of instability during the manufacturing process. Additionally, it is necessary to use a type of specific and expensive apparatus which adds to the high cost of the active principle and tends to increase the price of the finished product too much for large-scale worldwide use, the daily cost of treatment linked to the use of such a product being much more significant than that obtained by using a treatment of the type involving a bismuth salt and metronidazole or macrolide acting as an anti-acid and agents which destroy *Helicobacter pylori* (agent responsible for the majority of gastrointestinal ulcerations).

The subject of the invention overcomes these disadvantages. It relates to a new stable formulation of gastroprotected omeprazole microgranules and to the process which makes it possible to produce them under advantageous economic conditions.

According to the invention, omeprazole is used in the powder form diluted in a substantially equal amount of mannitol so as to produce a homogeneous and stable suspension and so as to provide better uniformity of the omeprazole content during application on neutral grains consisting of a mixture of sugar and of starch.

The present invention thus relates to a stable formulation of omeprazole microgranules, characterized in that they contain a neutral core consisting of sugar and of starch coated with an active layer comprising a dilution of omeprazole in mannitol in substantially equal amounts.

Dilute powder is understood to mean, according to the invention, a mixture of an omeprazole powder, of a mannitol powder, of sodium lauryl sulfate and of carboxymethylstarch.

Preferentially, the mixed powders have a substantially equal particle size of less than 100 microns.

Substantially equal amounts is understood to mean an omeprazole powder/mannitol powder ratio by weight in the region of 1, that is to say between 0.9 and 1.2.

The neutral cores consisting of sugar and of starch in proportions by weight in the region of 4 parts per 1 part of omeprazole powder have a mean diameter between 0.7 mm and 0.9 mm.

The layer of active principle, or active layer applied to the neutral grains, will preferably have a thickness between approximately 100 and 300 μm (0.1 and 0.3 mm).

To ensure good stability of the active principle during storage of the microgranules according to the invention, the moisture level of the active layer is less than 1%, preferably less than 0.5%.

Additionally, the microgranule according to the invention advantageously comprises an additional protective layer of the active layer consisting of mannitol and of a binding agent, in order to definitively isolate the core, on which the omeprazole is applied, from the external coating layer intended to provide gastroprotection of the active cores.

Preferentially, the binding agent is hydroxypropyl methylcellulose (HPMC) whereas the gastroresistant layer comprises hydroxypropyl methylcellulose phthalate (HPMCP) or anionic copolymers of methacrylic acid and talc.

In order to satisfy the in vitro dissolution criteria of the omeprazole microgranules, according to which at least 75% of the omeprazole must be dissolved after 30 minutes when the microgranules are placed in an aqueous medium with a pH equal to 6.8 and at a temperature of 37° C., the initial mixture of omeprazole and of mannitol is treated with approximately 10% of carboxymethylstarch (Explotab ®, marketed by the company Mendell), in order to produce complete disintegration of the granules at a pH equal to 6.8, and with approximately 5% of a surface-active agent, such as sodium lauryl sulfate, which improves solubilization of omeprazole in the intestinal medium.

Moreover, solutions, having a high viscosity of the order of 15 centipoises ($15 \times 10^{-3}$ Pa.s), of hydroxypropyl methylcellulose (HPMC) (Pharmacoat®, marketed by the company Shin-Etsu), used in solution in a mixture of at least 80% ethanol and at most 20% water, for example a mixture of 10 parts of water per 90 parts of 95° ethanol, and in small amounts in order to limit as far as possible the solvent and water content of the granules throughout the manufacture of the active granules, are used as binding solutions for applying the active layer to the neutral grains and then the additional mannitol protection.

Finally, according to an embodiment of the stable omeprazole granules according to the invention, the gastroresistant coating of the microgranules, consisting of hydroxypropyl methylcellulose phthalate (HPMCP) (HP 50 R, marketed by the Company Shin-Etsu) in 7.5% solution in an 80/20 mixture by mass of acetone and 95° ethanol, is applied in external layers after pretreatment of the active omeprazole and mannitol granules by spraying with a 33% sucrose syrup, in a 44/56 by mass water/ethanol mixture, this sugar syrup having a total sucrose weight of approximately 25% with respect to the amount of final gastroresistant coating. This external layer may contain talc as a lubricating agent.

Throughout all the various application and coating stages, the temperature of the granules is maintained between 32° C. and 38° C. and, between each stage, a drying is carried out so that the solvents and water contents are minimal, the final content being less than 1% for water and 2000 ppm for ethanol.

Other characteristics and advantages of the invention will become apparent in the light of the following examples.

EXAMPLE 1

Process for the preparation of micro granules containing 8.41% of omeprazole by weight All the amounts mentioned are expressed in kg of dry mass for a final amount equal to 237.80 kg of microgranules having an omeprazole content of 84.1 mg per gram of microgranules.

| COMPOSITION | |
|---|---|
| Neutral sugar and starch grains | 80.00 |
| Active layer: | |
| Omeprazole | 20.00 |
| Mannitol | 20.00 |
| Carboxymethylstarch (CMS) | 4.00 |
| Sodium lauryl sulfate | 2.00 |
| Additional protective layer: | |
| Mannitol | 50.00 |
| Sucrose | 8.00 |
| HPMC, 15 centipoises | 3.20 |
| Gastroresistant layer | |
| HPMCP | 32.00 |
| Talc | 18.60 |

| COMPOSITION | |
|---|---|
| -continued | |
| | 237.80 |

The process, according to the invention, consists in preparing a dilution of 20 kg of omeprazole in 20 kg of mannitol in the presence of 4 kg of CMS and of 2 kg of sodium lauryl sulfate, and then binding this dry dilution onto 80 kg of neutral sugar and starch grains, whose diameter is between 0.7 and 0.9 mm, with the aid of a 4% solution of HPMC (1.6 kg) in water (20 parts) and 95° ethanol (80 parts) in a circular turbine with an inclined flat bottom, and then protecting the active grains thus obtained with the aid of 50 kg of mannitol applied with the rest of the HPMC solution (i.e. 1.6 kg), and then pretreating the granules thus protected with a 33% sugar syrup (8 kg of sucrose) consisting of 44 parts of water per 56 parts of 95° ethanol and in finally applying the gastroprotection coating at a charge of 32 kg of HPMCP in 7.5% solution in a mixture of 80 parts of 95° ethanol per 20 parts of acetone.

The granules thus obtained show a gastroresistance of greater than 85% in a medium with a pH of 1.2, since, after 2 hours at 37° C., the amount of unreleased omeprazole in this medium is 91.7%. In an aqueous medium with a pH equal to 6.8, the dissolution of the granules shows, after 30 minutes, an omeprazole degree of 92%, i.e. an amount greater than 75% which is the minimum acceptable standard.

At the end of 12 and 24 months, the respective gastroresistance values are 92.1% and 92.8% and the dissolutions at a pH of 6.8 are 91.4% and 93.8% under the same operating conditions.

Moreover, the very-pale beige color of the microgranules stored in gelatin capsules at room temperature and an external humidity of 60% in glass bottles fitted with protective caps and containing desiccating capsules is maintained constant for a period of at least 24 months.

EXAMPLE 2

Stability Tests

The testing of the stability of omeprazole was carried out on 4 batches of gelatin capsules comprising microgranules according to the invention and one batch of microgranules. The monitored batches, the storage conditions, the methods of analyses and the results are presented below.

1. MONITORED BATCHES
Omeprazole gelatin capsules
C458-1-2, C458-1-6, C458-2-3 and C458-2-4
Omeprazole microgranules
UQM 001-3

| BATCHES | DATES OF MANUFACTURE | STORAGE TIME (months) |
|---|---|---|
| C458-1-2 | June 1983 | 36 |
| C458-1-6 | February 1984 | 36 |
| C458-2-3 | September 1984 | 24 |
| C458-2-4 | October 1984 | 24 |
| UQM 001-3 | October 1990 | 3 |

2. STORAGE CONDITIONS
25° C.-60% Relative humidity
30° C.-30–40%, 60% Relative humidity
37° C.-20–30%, 90% Relative humidity 50° C.-80% Relative humidity
Refrigerator

3. ANALYSIS OF THE SAMPLES a. gelatin capsules

Sample solution

A - For the quantitative determination of omeprazole, introduce the contents of 5 gelatin capsules into a 250 ml volumetric flask, then introduce 200 ml of methanol-/aqueous ammonia (95/5) solution and stir magnetically for 30 minutes. Complete to volume using the same solvent. Filter and dilute 10 ml of the filtrate in a 100 ml volumetric flask with 30 ml of dichloromethane and complete to volume using a methanol/aqueous ammonia/dichloromethane (24/1/75) solution.

B - To determine the degradation products, dissolve the contents of 2 gelatin capsules in 8 ml of the methanol/aqueous ammonia (95/5) solution, with magnetic stirring for 30 minutes. Filter and dilute 2.5 ml of the filtrate to 100 ml in dichloromethane. Inject immediately.

Equipment and conditions

HPLC apparatus equipped with a U.V. detector.

7 μm silica precolumn with a length of 15 mm and an internal diameter of 3.2 mm (Brownlee or equivalent).

5 μm Lichrosorb Si 60 column, with a length of 124 mm and an internal diameter of 4 mm (Hibar Merck or equivalent).

Flow rate: 1 ml/min.
Reading at 280 nm
Injection: 40 μl.

Monitoring of the system

Once stability of the baseline has been obtained, the system is monitored in the following way:

Dissolve 5 mg of omeprazole standard and 5 mg of the corresponding sulfone H 168/66 (whose formula is reproduced below) in 100 ml of the mobile phase. Inject 40 μl several times until a constant retention time is obtained (difference between two injections <1%).

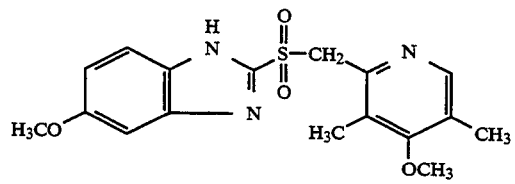

The retention time of omeprazole is 10 minutes and that of the sulfone H 168/66 is 8 minutes.

b. microgranules

Determination of the omeprazole content of the microgranules

The omeprazole content of the microgranules is determined by ultraviolet spectrophotometry after separation by high performance liquid chromatography.

Reagents

Acetonitrile for HPLC (for example Carlo Erba ref. 412409)

Dibasic sodium phosphate ($Na_2HPO_4$)
Monobasic sodium phosphate ($NaH_2PO_4.H_2O$)
Distilled water
Reference substance: omeprazole Equipment Apparatus for liquid chromatography with a UV detector (280 nm):
2 stainless steel columns in series:

precolumn: length 1.5 cm - internal ⌀3.2 mm - particle size 7 μm column: length 12.5 cm - internal ⌀4 mm - particle size 5 μm Stationary phase: Lichrosorb RP 18

Injection system: for 20 μl amounts (for example Wisp 712 automatic injector).

Integrator: Perkin Elmer LCI 100 or Waters 645 Data Module

Gastroresistance and dissolution tests

The microgranules are stirred for 2 h 30 in suitable media at constant temperature (37° C.±0.5° C.) in a dissolution apparatus.

Equipment

The dissolution apparatus used is the paddle apparatus described in the European Pharmacopeia.

Speed used: 500 ml of medium with a pH of 1.2. Addition of 400 ml of medium with a pH of 7.6.

Media

Medium I: Medium having acid strength:

Introduce 2 grams of sodium chloride and 7 ml of concentrated (37%) hydrochloric acid into a 1 liter volumetric flask. Complete to volume using purified water. Stir until dissolved. The pH of this solution should be 1.2±0.05.

Medium II: Medium with a pH of 7.6 (addition)

0.235M Dibasic sodium phosphate solution ($Na_2HPO_4$). Prepare 1 liter of solution for 2 vessels.

4. RESULTS AND CONCLUSIONS

The results are summarized in the tables below.

During determination of the impurities content, two main impurities are detected in all the batches. In the tables of results, they are identified by the designations I and I'.

A: Storage period (months)
B: Storage conditions - °C. - Relative humidity
C: Appearance
D: Disintegration (min)
E: Omeprazole assay (mg/gel)

| Omeprazole gelatin capsules, batch C458-1-2 | | | | | | | |
|---|---|---|---|---|---|---|---|
| | | | | | | F | |
| | | | | | I | I' | Others |
| A | B | C | D | E | % | % | % |
| 0 | | | a | 6 | 20.3 | <0.5 | <0.5 | <0.2 |
| 6 | 25 | 60 | a | 5 | 20.6 | <0.5 | <0.5 | <0.2 |
| | 30 | 60 | a | 7 | 20.1 | <0.5 | <0.5 | <0.2 |
| | 50 | 80 | c | 7 | 19.4 | <0.5 | <0.5 | <0.3 |
| 12 | 25 | 60 | a | 5 | 20.5 | <0.5 | <0.5 | <0.2 |
| | 30 | 60 | b | 6 | 20.5 | <0.5 | <0.5 | <0.2 |
| 18 | 25 | 60 | a | 6 | 19.8 | <0.5 | <0.5 | <0.2 |
| | 30 | 60 | b | 6 | 20.1 | <0.5 | <0.5 | <0.2 |
| 24 | 25 | 60 | a | 6 | 20.7 | <0.5 | <0.5 | <0.2 |
| | 30 | 60 | c | 7 | 20.2 | <0.5 | <0.5 | <0.3 |
| 30 | 25 | 60 | a | 6 | 20.3 | <0.5 | <0.5 | <0.3 |
| 36 | 25 | 60 | b | 6 | 19.9 | <0.5 | <0.5 | <0.3 |
| refrigerator | | | a | 6 | 20.8 | <0.5 | <0.5 | <0.2 | a = white,
b = colored, conforms,
c = colored, does not conform

| Omeprazole gelatin capsules, batch C458-1-6 | | | | | | | |
|---|---|---|---|---|---|---|---|
| | | | | | | F | |
| | | | | | I | I' | Others |
| A | B | C | D | E | % | % | % |
| 0 | | | a | 5 | 19.4 | <0.5 | <0.5 | <0.2 |
| 6 | 25 | 60 | a | 5 | 19.6 | <0.5 | <0.5 | <0.2 |
| | 30 | 60 | a | 6 | 19.5 | <0.5 | <0.5 | <0.2 |
| | 50 | 80 | c | 7 | 18.7 | <0.5 | <0.5 | <0.4 |

-continued

Omeprazole gelatin capsules, batch C458-1-6

| A | B | C | D | E | F I % | F I' % | F Others % |
|---|---|---|---|---|---|---|---|
| 12 | 25 | 60 | a | 5 | 19.2 | <0.5 | <0.5 | <0.2 |
|    | 30 | 60 | b | 6 | 19.3 | <0.5 | <0.5 | <0.2 |
| 18 | 25 | 60 | a | 5 | 19.7 | <0.5 | <0.5 | <0.2 |
|    | 30 | 60 | b | 5 | 19.1 | <0.5 | <0.5 | <0.3 |
| 24 | 25 | 60 | a | 6 | 19.0 | <0.5 | <0.5 | <0.2 |
|    | 30 | 60 | c | 6 | 19.2 | <0.5 | <0.5 | <0.3 |
| 30 | refrigerator | | a | 6 | 19.8 | <0.5 | <0.5 | <0.2 |
|    | 25 | 60 | a | 5 | 19.3 | <0.5 | <0.5 | <0.2 |
| 36 | refrigerator | | a | 6 | 19.8 | <0.5 | <0.5 | <0.2 |
|    | 25 | 60 | b | 5 | 19.2 | <0.5 | <0.5 | <0.2 | a = white,
b = colored, conforms,
c = colored, does not conform

Omeprazole gelatin capsules, batch C458-2-3

| A | B | C | D | E | F I % | F I' % | F Others % |
|---|---|---|---|---|---|---|---|
| 0 | | | a | <5 | 21.2 | <0.5 | <0.5 | <0.2 |
| 6 | refrigerator | | a | <5 | 20.9 | <0.5 | <0.5 | <0.2 |
|   | 25 | 60 | a | 5 | 21.1 | <0.5 | <0.5 | <0.2 |
| 12 | refrigerator | | a | 5 | 20.8 | <0.5 | <0.5 | <0.2 |
|    | 25 | 60 | a | <5 | 20.7 | <0.5 | <0.5 | <0.2 |
| 18 | refrigerator | | a | <5 | 20.6 | <0.5 | <0.5 | <0.2 |
|    | 25 | 60 | a | 5 | 20.4 | <0.5 | <0.5 | <0.2 |
| 24 | 25 | 60 | a | 6 | 20.7 | <0.5 | <0.5 | <0.2 | a = white,
b = colored, conforms,
c = colored, does not conform

Omeprazole gelatin capsules, batch C458-2-4

| A | B | C | D | E | F I % | F I' % | F Others % |
|---|---|---|---|---|---|---|---|
| 0 | | | | 6 | 20.7 | <0.5 | <0.5 | <0.2 |
| 6 | 25 | 60 | a | <5 | 20.8 | <0.5 | <0.5 | <0.2 |
| 12 | 25 | 60 | a | 5 | 20.3 | <0.5 | <0.5 | <0.2 |
| 18 | 25 | 60 | a | 6 | 20.5 | <0.5 | <0.5 | <0.2 |
| 24 | refrigerator | | a | 5 | 20.0 | <0.5 | <0.5 | <0.2 |
|    | 25 | 60 | b | 5 | 20.4 | <0.5 | <0.5 | <0.5 | a = white,
b = colored, conforms,
c = colored, does not conform

Omeprazole microgranules, UQM 001-3
A: Storage period (months)
B: Storage conditions - °C. - Relative humidity
C: Appearance
D: Omeprazole assay (mg/g)
E: Gastroresistance test
F: Dissolution test - %

| A | B | | C | D | E | F |
|---|---|---|---|---|---|---|
| 0 | | | a | 78.0 | 95.9 | 95.0 |
| 1 | 25 | 55–65 | a | 80.8 | 93.9 | 94.0 |
|   | 30 | 30–40 | a | 81.2 | 94.4 | 95.0 |
|   | 37 | 20–40 | a | 80.4 | 97.0 | 97.0 |
|   | 37 | 90 | a | 77.6 | 97.5 | 100.0 |
| 3 | 25 | 56–65 | a | 81.4 | 91.6 | 92.0 |
|   | 30 | 30–40 | a | 79.1 | 95.7 | 96.0 |
|   | 37 | 20–40 | a | 80.2 | 92.0 | 93.0 |
|   | 37 | 90 | c | 41.9 | — | — | a = white,
b = colored, conforms,
c = colored, does not conform

The gelatin capsules have good stability in the refrigerator and at 25° C., for up to 36 months of storage. All the impurities have a concentration of less than 0.50%.

The impurities content increases a little more with temperature and humidity, and can be sufficient to cause coloration of the granules.

The microgranules stored in bulk have good stability for 3 months at room temperature and 55–65% relative humidity, at 30° C. and 30–40% relative humidity and at 37° C. and 20–30% relative humidity, and for month at 37° C. and 90% relative humidity.

TERM OF VALIDITY

In the light of the results obtained, the specialty is stable for 36 months provided that it does not exceed 25° C. during this period.

| SPECIFICATIONS | |
|---|---|
| 1. Appearance | hard gelatin capsules containing off-white to more or less dark-beige granules without foreign particles. |
| 2. Mean weight | approximately 235 mg ± 10% |
| 3. Omeprazole content | 18.0–22.0 mg/gelatin capsule (90–110%) |
| 4. Resistance in acid medium | ≧85% |
| 5. Release at a pH of 6.8 | ≧75% |
| 6. Degradation products | total content ≦2.0% individual contents ≦0.5% |

Of course, a person skilled in the art will be able to introduce variants into the embodiments of the microgranules according to the invention, in particular by using coating apparatuses such as fluidized beds in place of the flat-bottomed turbines described above, or also by using methacrylic polymers as gastroprotection materials (for example Eudragit ® L 100-55 or L 30 D of the company Rohm & Hass) or other gastroresistant polymers, without departing from the context and scope of the invention.

On the other hand, the invention is not intended to produce microgranules by the conventional extrusion techniques already described in the prior art, these techniques requiring the use of omeprazole in solution in a mass containing solvents and water, which are avoided by virtue of the embodiments of the process described above in order to overcome the consequences of the instability of omeprazole under such conditions.

We claim:

1. A stable formulation of omeprazole microgranules containing a neutral core of sugar and starch and an active layer consisting of a dilution of omeprazole in mannitol in substantially equal amounts, wherein the active omeprazole layer contains about 10% by weight of carboxymethylstarch, about 5% by weight of a sodium lauryl sulfate surface-active compound, and wherein the dilution of omeprazole in mannitol is applied to the neutral core by means of hydroxypropyl methylcellulose as a high viscosity binder.

2. The formulation as claimed in claim 1, wherein the formulation contains, at the surface of the active omeprazole layer, an additional protective layer consisting of mannitol.

3. The formulation as claimed in claim 2, wherein said protective layer is applied by means of a high viscosity binder of hydroxypropyl methylcellulose.

4. The formulation as claimed in claim 1, wherein the active grains contain an external gastroprotection layer consisting of a gastroresistant coating of hydroxypropyl methylcellulose phthalate and talc.

5. A process for producing the formulations as claimed in claim 1, wherein a dry dilution of mannitol and of omeprazole is applied to neutral grains consisting of sugar and of starch with the aid of a high-viscosity binding solution of hydroxypropyl methylcellulose in solution in a mixture of at least 80% ethanol and at most 20% water.

6. The process as claimed in claim 5, wherein each application of the dry dilution is followed by drying at a temperature between 35° C. and 40° C. for a time which makes it possible to lower the water content of the active microgranules to 1% and their ethanol content to 2000 ppm.

7. The process as claimed in claim 5, wherein neutral microgranules are used whose size is between 0.7 and 0.9 mm.

8. The process as claimed in claim 5, wherein flat-bottomed turbines are used to carry out the active dilution applications and the gastroprotection coatings.

* * * * *